United States Patent
Chen et al.

(10) Patent No.: US 11,345,941 B2
(45) Date of Patent: May 31, 2022

(54) METHOD FOR PREPARING (S)-1-BENZYL-1,2,3,4,5,6,7,8-OCTAHYDROISOQUINOLINE COMPOUND

(71) Applicant: FUDAN UNIVERSITY, Shanghai (CN)

(72) Inventors: Fener Chen, Shanghai (CN); Zedu Huang, Shanghai (CN); Zhining Li, Shanghai (CN); Jiaqi Wang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 146 days.

(21) Appl. No.: 16/805,742

(22) Filed: Feb. 29, 2020

(65) Prior Publication Data
US 2021/0087595 A1    Mar. 25, 2021

(30) Foreign Application Priority Data
Sep. 20, 2019   (CN) .......................... 201910890595.5

(51) Int. Cl.
| | | |
|---|---|---|
| C12P 17/12 | (2006.01) | |
| C12N 9/06 | (2006.01) | |
| C12P 41/00 | (2006.01) | |

(52) U.S. Cl.
CPC ....... *C12P 17/12* (2013.01); *C12Y 104/03004* (2013.01); *C12P 41/006* (2013.01)

(58) Field of Classification Search
CPC .. C07D 207/14; C07D 405/10; C07C 233/80; C07C 235/56; C07C 271/20; C07C 271/22; C12P 17/12; C12P 41/006; C12Y 104/03004

USPC ......... 435/133, 156, 191; 514/432, 459, 466
See application file for complete search history.

(56) References Cited

FOREIGN PATENT DOCUMENTS

| CN | 103319406 A | 9/2013 |
|---|---|---|
| CN | 107056700 A | 8/2017 |
| CN | 108003099 A | 5/2018 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*

* cited by examiner

*Primary Examiner* — Robert B Mondesi
*Assistant Examiner* — Mohammad Y Meah

(57) ABSTRACT

This application relates to biological pharmacy and biochemical engineering, and more particularly to a method of preparing a (S)-1-benzyl-1,2,3,4,5,6,7,8-octahydroisoquinoline compound. This method includes: subjecting a 1-benzyl-1,2,3,4,5,6,7,8-octahydroisoquinoline raceme as a substrate to selective oxidation in the presence of a monoamine oxidase and the non-selective reduction to prepare the (S)-1-benzyl-1,2,3,4,5,6,7,8-octahydroisoquinoline compound, where the monoamine oxidase has an amino acid sequence as shown in SEQ ID NO: 1 or an amino acid sequence having an identity of more than 80% with SEQ ID NO: 1. The kinetic resolution is carried out in the presence of the monoamine oxidase as a catalyst and a reductant, and the resulting product has a high chiral purity.

10 Claims, 3 Drawing Sheets
Specification includes a Sequence Listing.

Raceme

Enzymatic reaction product

METHOD FOR PREPARING (S)-1-BENZYL-1,2,3,4,5,6,7,8-OCTAHYDROISOQUINOLINE COMPOUND

REFERENCE TO AN ELECTRONIC SEQUENCE LISTING

The contents of the electronic sequence listing (Untitled_ST25.txt; Size: 5,000 bytes; and Date of Creation: May 5, 2020) is herein incorporated by reference in its entirety.

CROSS-REFERENCE TO RELATED APPLICATIONS

This application claims the benefit of priority from Chinese Patent Application No. 201910890595.5, filed on Sep. 20, 2019. The content of the aforementioned application, including any intervening amendments thereto, is incorporated herein by reference in its entirety.

TECHNICAL FIELD

This application relates to biological pharmacy and biochemical engineering, more particularly to a method for preparing a (S)-1-benzyl-1,2,3,4,5,6,7,8-octahydroisoquinoline compound.

BACKGROUND (S)-1-benzyl-1,2,3,4,5,6,7,8-octahydroisoquinoline compounds are an important class of chiral compounds, which have the structure of formula (I), where $R^1$ and $R^2$ are each independently selected from hydrogen, $C_1$-$C_6$ alkyl and cycloalkyl, $C_1$-$C_6$ alkoxyl, halogen, cyano, nitro, hydroxyl, amino, methylthio, $C_1$-$C_6$ ester group and trifluoromethyl. Among the (S)-1-benzyl-1,2,3,4,5,6,7,8-octahydroisoquinoline compounds, (S)-1-(4-methoxybenzyl)-1,2,3,4,5,6,7,8-octahydroisoquinoline (II) and N-methylated products thereof are crucial intermediates during the preparation of an antitussive drug dextromethorphan hydrobromide (Chinese Patent Application Nos. 201310041846 and 201210405684). Currently, the compound (II) is generally prepared by kinetic chiral resolution, but this process has a yield of less than 50% and produces three-waste pollution (Chinese Patent Application No. 201210073513 and U.S. Pat. No. 8,148,527). Moreover, Dunming Zhu et al. (Chinese Patent Application No. 201510875024 and Sci. Rep., 2016, 6, 24973) disclose a method for preparing (S)-1-(4-methoxybenzyl)-1,2,3,4,5,6,7,8-octahydroisoquinoline (II) by kinetic resolution with the combination of monoamine oxidase and non-selective chemical reductant, which has a yield of 78% and an optical purity greater than 99% ee. However, this method has an extremely low substrate concentration (only 2.6 g/L, i.e., a mass concentration of 0.26%), thus limiting its industrial application.

Given the above, this application provides herein a method of preparing (S)-1-benzyl-1,2,3,4,5,6,7,8-octahydroisoquinoline compound (I) through the combination of a newly-developed monoamine oxidase and a non-selective chemical reductant, which can be specifically applied in the preparation of (S)-1-(4-methoxybenzyl)-1,2,3,4,5,6,7,8-octahydroisoquinoline (II) by kinetic resolution. This method has characteristics of high substrate concentration, high yield of separation, simple operation and mild reaction conditions.

SUMMARY

An object of this application is to provide a method of preparing a (S)-1-benzyl-1,2,3,4,5,6,7,8-octahydroisoquinoline compound, which has the advantages of desirable substrate concentration, high yield and excellent stereoselectivity and being environmentally friendly.

This application provides a method of preparing a (S)-1-benzyl-1,2,3,4,5,6,7,8-octahydroisoquinoline compound of formula (I)

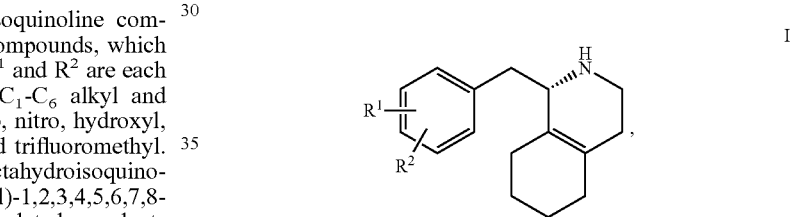

comprising: subjecting a 1-benzyl-1,2,3,4,5,6,7,8-octahydroisoquinoline raceme as a substrate to kinetic resolution in the presence of the monoamine oxidase as a catalyst and a non-selective chemical reductant to prepare the (S)-1-benzyl-1,2,3,4,5,6,7,8-octahydroisoquinoline compound, as shown in the following reaction route:

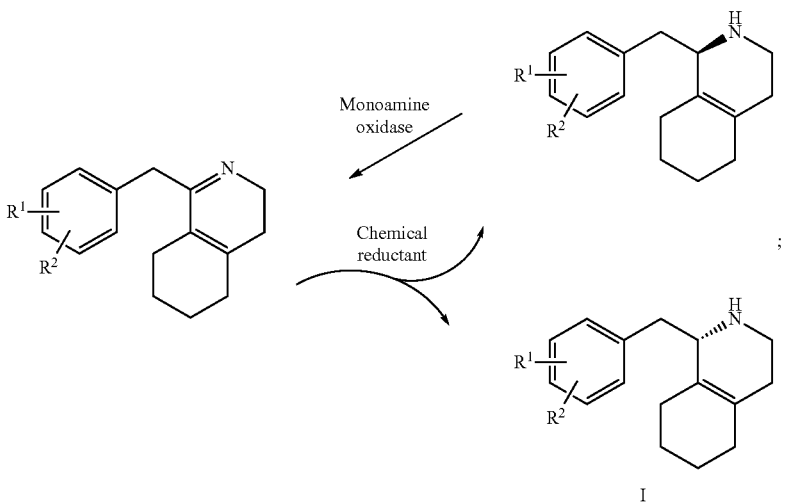

wherein $R^1$ and $R^2$ are each independently selected from hydrogen, $C_1$-$C_6$ alkyl and cycloalkyl, $C_1$-$C_6$ alkoxyl, halogen, cyano, nitro, hydroxyl, amino, methylthio, $C_1$-$C_6$ ester group and trifluoromethyl.

In an embodiment, the monoamine oxidase is expressed using a conventional *E. coli* expression system.

In an embodiment, the monoamine oxidase has an amino acid sequence shown as SEQ ID NO:1 or an amino acid sequence having an identity with SEQ ID NO:1 of more than 80%.

In some embodiments, a variant amino acid sequence shows an identity with SEQ ID NO:1 of at least 80%, 81%, 82%, 83%, 84%, 85%, 86%, 87%, 88%, 89%, 90%, 91%, 92%, 93%, 94%, 95%, 96%, 97%, 98% or 99%. A small number of amino acid residues at particular positions, for example W63, I173, L174, L200, I201, G202, T203, Q208, L295, F317, W325, F327, F342, P396 or Y433 may be altered without affecting the catalytic activity of the enzyme. Changes (e.g., deletion or substitution) can be made to one or more of amino acid residues W63, I173, L174, L200, I201, G202, T203, Q208, L295, F317, W325, F327, F342, P396 and Y433. These variants should fall within the scope of the invention.

In an embodiment, the amino acid sequence of the monoamine oxidase can be synthesized by commercial whole gene synthesis.

In an embodiment, the monoamine oxidase is in a form of a genetically engineered whole cell, a crude enzyme solution, a pure enzyme or an immobilized enzyme.

In an embodiment, the monoamine oxidase can be prepared by a conventional method in the art, which comprises the steps of: ligating a monoamine oxidase gene-containing fragment with a digested product of the pET-28a plasmid; transforming the ligated product into competent *E. coli* DH5 cells to obtain a recombinant; and subjecting the recombinant to transformation, induced expression and centrifugation to give a wet cell, that is, a monoamine oxidase whole cell catalyst.

In an embodiment, the non-selective reductant is for reducing an amine.

In an embodiment, the non-selective reductant is selected from the group consisting of boranamine and sodium borohydride.

In an embodiment, a molar equivalent ratio of the non-selective reductant to the 1-benzyl-1,2,3,4,5,6,7,8-octahydroisoquinoline raceme is 1-10:1, preferably 4-10:1.

In an embodiment, the 1-benzyl-1,2,3,4,5,6,7,8-octahydroisoquinoline raceme has a concentration of 0.1%-5% (w/v), preferably 1%-3% (w/v).

In an embodiment, the monoamine oxidase, calculated as wet cells, is 300%-1000% by weight of the 1-benzyl-1,2,3,4,5,6,7,8-octahydroisoquinoline raceme, preferably 500%-1000%.

In an embodiment, a reaction temperature is 15-50° C., preferably 25-37° C.; and a reaction time is 6-72 h.

In an embodiment, a pH of the reaction mixture is 6-10, preferably 7-8.

In an embodiment, this method further comprising: terminating the reaction with 1-6 M hydrochloric acid; adjusting pH of the reaction mixture to 10-11 with 1-10 M sodium hydroxide; extracting the reaction mixture with ethyl acetate 3-5 times by high-speed centrifugation and collecting and combining the organic phases; drying the combined organic phase with anhydrous sodium sulfate; and purifying the dried organic phase by column chromatography to give the (S)-1-benzyl-1,2,3,4,5,6,7,8-octahydroisoquinoline compound.

Compared with the prior art, this application has the following beneficial effects.

The method provided herein has high substrate concentration, simple operation, mild reaction conditions and excellent stereoselectivity, and is environmentally friendly, having desirable industrial application prospects.

DETAILED DESCRIPTION OF EMBODIMENTS

This application will be further illustrated below with reference to the embodiments, but is not limited thereto.

Example 1 Expression of Monoamine Oxidase

A monoamine oxidase gene-containing pET-28a plasmid was transformed into competent *E. coli* BL21 (DE3) cells. The transformed cells were screened to obtain positive clones, which were inoculated into 5 mL of a kanamycin-containing liquid LB medium and activated at 37° C. and 200 rpm for 8 h. Then the activated cells were inoculated into 500 mL of the kanamycin-containing liquid LB medium at a volume ratio of 1:100 and cultured at 37° C. and 200 rpm to an $OD_{600}$ of 0.6-0.8. IPTG was added to a final concentration of 0.1 mM and the cells were cultured at 18° C. under shaking at 200 rpm for 18 h. The culture system was centrifuged and the cells were washed once with phosphate buffer (50 mM, pH 7.5) and collected (wet cells).

Example 2 Preparation of (S)-1-(4-methoxybenzyl)-1,2,3,4,5,6,7,8-octahydroisoquinoline (II) by Enzymatic Kinetic Resolution (50 g/L of a Substrate)

Figure 1:
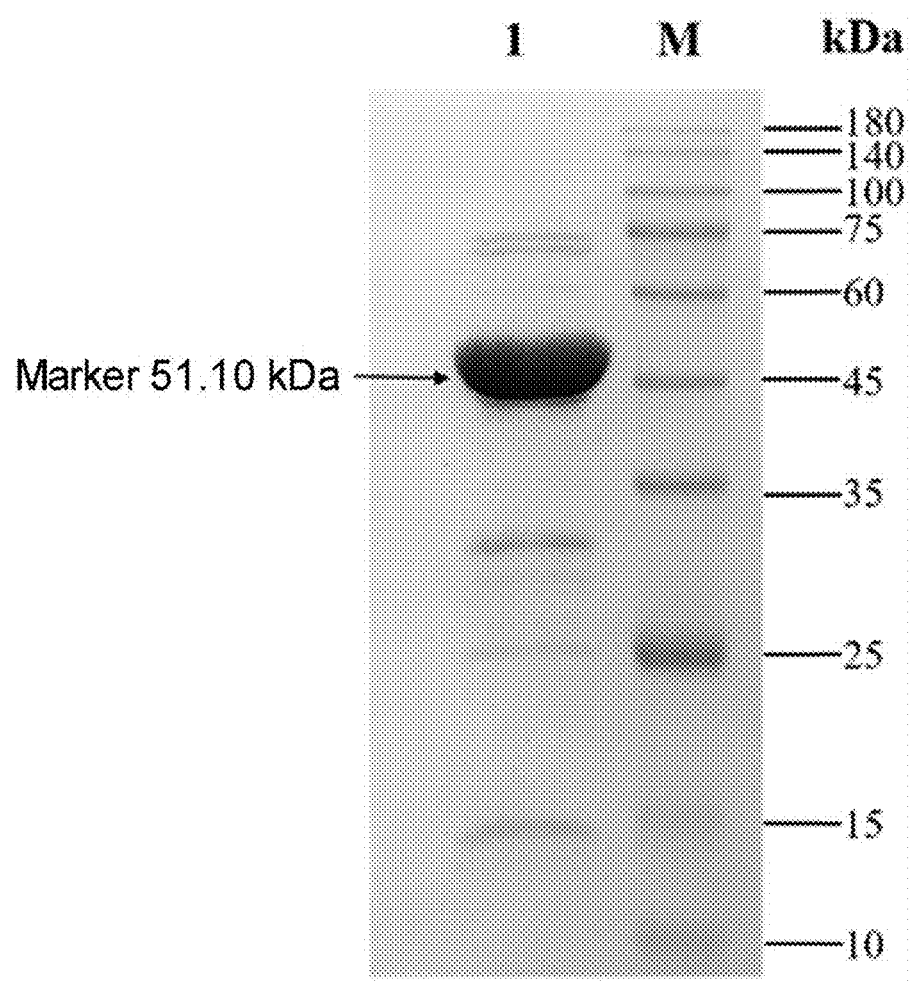
FIG. 1 is a SDS-PAGE electropherogram of a monoamine oxidase of the invention, in which, M: Marker; and 1: the purified monoamine oxidase.
Figure 2A:
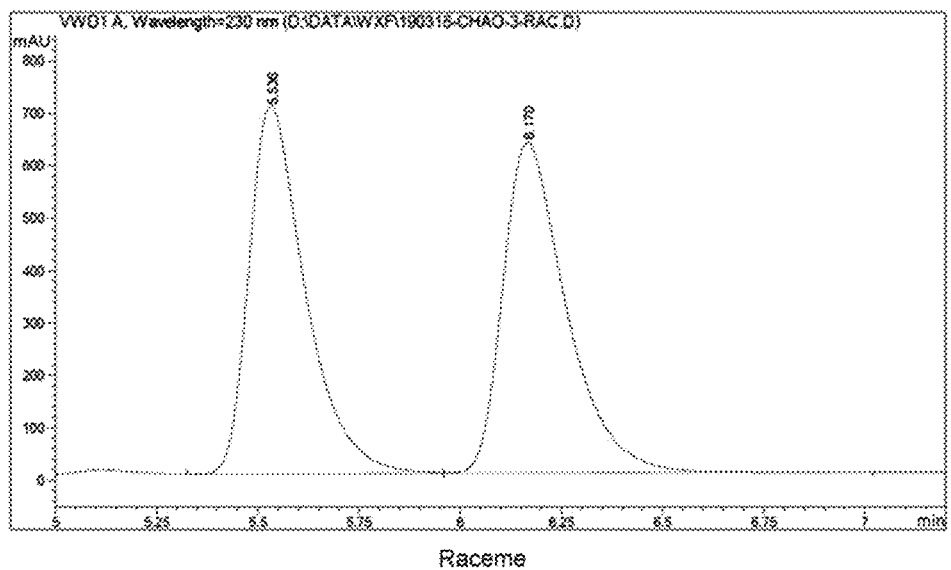
FIGS. 2A-B are chiral HPLC spectrograms of the (S)-1-(4-methoxybenzyl)-1,2,3,4,5,6,7,8-octahydroisoquinoline raceme and the purified (S)-1-(4-methoxybenzyl)-1,2,3,4,5,6,7,8-octahydroisoquinoline (II) according to Example 2 of the present invention.
Figure 2B:
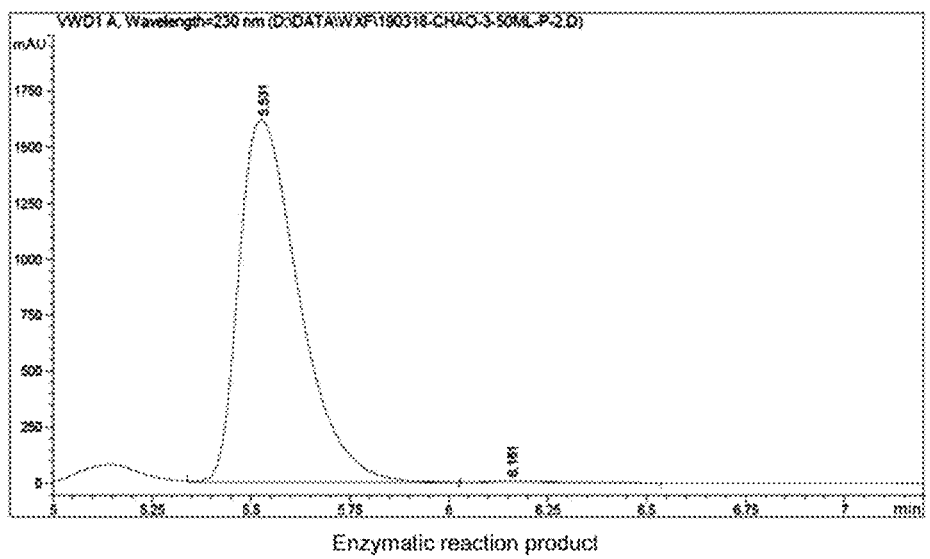

To 50 mL of a cell suspension were added 2.5 g of a 1-(4-methoxybenzyl)-1,2,3,4,5,6,7,8-octahydroisoquinoline raceme and 1.65 g of boranamine, where the cell suspension was prepared by resuspending 10 g of wet cells collected after centrifugation in 50 mM phosphate buffer (pH 7.5). The reaction mixture was reacted at 35° C. and 600 rpm. 24 h later, when the reaction was determined by LC to be completed, 1 M hydrochloric acid was introduced to terminate the reaction, and the reaction mixture was adjusted to pH 10 with 3 M sodium hydroxide and extracted three times with ethyl acetate by high-speed centrifugation (100 mL×3). The organic phases were combined, dried with anhydrous sodium sulfate and then purified by column chromatography to give 2.02 g of a product (81% yield), where the optical test results showed that the product had $[\alpha]^{20}_D$ of −125.01 (c=1.0, methanol, 1=100 mm) and a reference value in Chinese patent No. 201510875024 was −130 (c=1.0, methanol). Then the product was analyzed by LC to have an ee value of 99%, where the detection parameters were described as follows: OJ-H column; mobile phase: a mixture of n-hexane and isopropanol (containing 0.5% ethanolamine) in a ratio of 90:10; flow rate: 0.8 mL/min; column temperature: 30° C.; and wavelength: 230 nm. The LC results were shown in FIGS. 2A-2B.

$^1$H NMR (DMSO-$d_6$, 400 MHz): δ/ppm 7.14 (d, J=8.4 Hz, 2H), 6.85 (d, J=8.4 Hz, 2H), 3.73 (s, 3H), 3.12 (d, J=9.3 Hz, 1H), 2.94-2.81 (m, 2H), 2.65-2.55 (m, 1H), 2.38 (dd, J=13.4, 10.1 Hz, 1H), 2.09 (d, J=14.6 Hz, 1H), 1.92-1.76 (m, 4H), 1.72-1.59 (m, 2H), 1.54-1.42 (m, 2H).

$^{13}$C NMR (DMSO-$d_6$, 100 MHz): δ/ppm 157.96, 132.59, 130.88, 130.59, 128.02, 114.02, 58.76, 55.42, 40.38, 37.99, 31.16, 30.42, 27.01, 23.33, 22.99.

Example 3 Preparation of (S)-1-(3-fluorobenzyl)-1,2,3,4,5,6,7,8-octahydroisoquinoline by Enzymatic Kinetic Resolution (30 g/L of a Substrate)

Figure 3A:
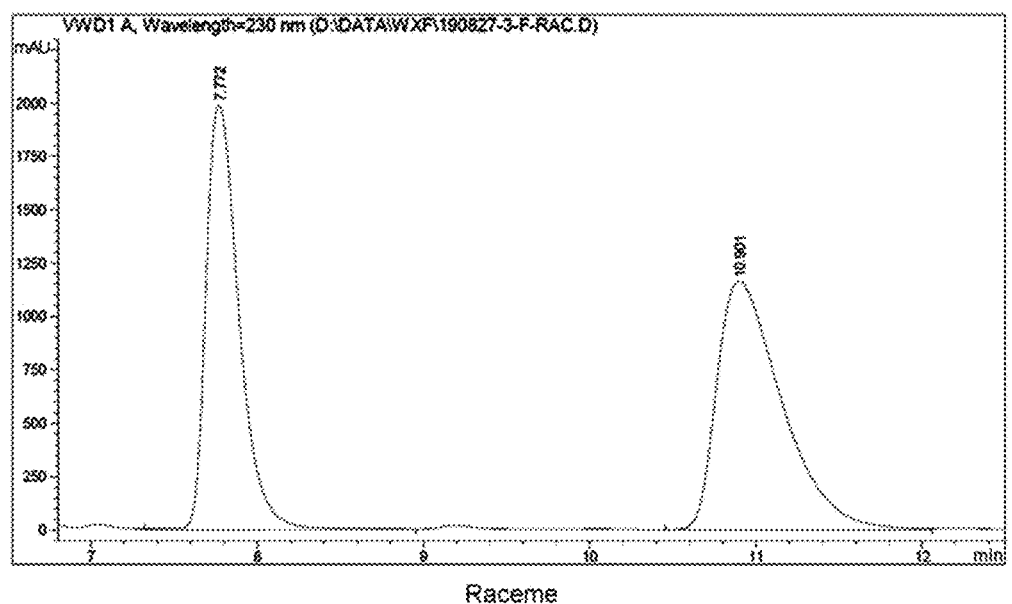
FIGS. 3A-B are chiral HPLC spectrograms of the (S)-1-(3-fluorobenzyl)-1,2,3,4,5,6,7,8-octahydroisoquinoline raceme and the purified (S)-1-(3-fluorobenzyl)-1,2,3,4,5,6,7,8-octahydroisoquinoline according to Example 3 of the present invention.
Figure 3B:
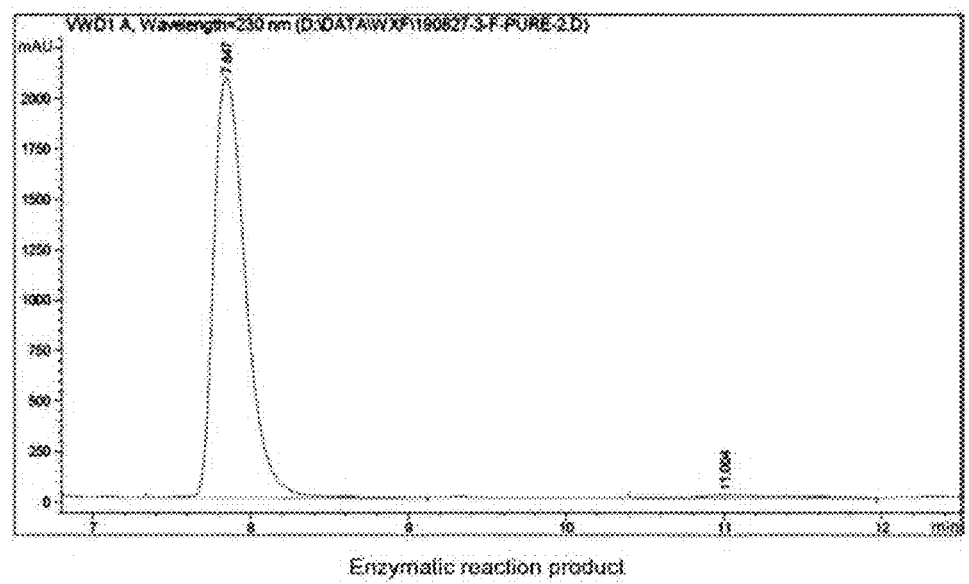

To 12.7 mL of a cell suspension were added 381 mg of a 1-(3-fluorobenzyl)-1,2,3,4,5,6,7,8-octahydroisoquinoline raceme and 216 mg of boranamine, where the cell suspension was prepared by resuspending 2.54 g of wet cells collected after centrifugation in 50 mM phosphate buffer (pH 7.5). The reaction mixture was reacted at 35° C. and 600 rpm. 72 h later, when the reaction was determined by LC to be completed, 1 M hydrochloric acid was introduced to terminate the reaction, and the reaction mixture was adjusted to pH 10 with 3 M sodium hydroxide and extracted three times with ethyl acetate by high-speed centrifugation (100 mL×3). The organic phases were combined, dried with anhydrous sodium sulfate and then purified by column chromatography to give 237 mg of a product (62% yield), where the optical test results showed that the product had $[α]^{25}_D$ of −145.30 (c=0.5, methanol, 1=100 mm). Then the product was analyzed by LC to have an ee value of 97%, where the detection parameters were described as follows: AD-H column; mobile phase: a mixture of n-hexane and isopropanol (containing 0.5% ethanolamine) in a ratio of 95:5; flow rate: 0.5 mL/min; column temperature: 25° C.; and wavelength: 230 nm. The LC results were shown in FIGS. 3A-B.

$^1$H NMR (DMSO-$d_6$, 400 MHz): δ/ppm 7.28 (q, J=7.7 Hz, 1H), 7.10-6.93 (m, 3H), 3.17 (d, J=9.9 Hz, 1H), 2.94-2.82 (m, 2H), 2.64-2.54 (m, 1H), 2.45 (dd, J=13.4, 10.1 Hz, 1H), 2.05 (d, J=15.7 Hz, 1H), 1.90-1.72 (m, 4H), 1.70-1.56 (m, 2H), 1.52-1.39 (m, 2H).

$^{13}$C NMR (DMSO-$d_6$, 100 MHz): δ/ppm 162.55 (d, J=242.5 Hz), 144.02 (d, J=7.5 Hz), 130.78, 130.18 (d, J=8.4 Hz), 128.34, 125.81 (d, J=2.5 Hz), 116.35 (d, J=20.6 Hz), 112.90 (d, J=20.9 Hz), 58.38, 40.32, 38.57, 31.04, 30.46, 26.96, 23.32, 22.97.

Example 4 Preparation of (S)-1-(3, 4-dimethoxybenzyl)-1,2,3,4,5,6,7,8-octahydroisoquinoline by Enzymatic Kinetic Resolution (30 g/L Substrate)

To 10 mL of a cell suspension were added 405 mg of a 1-(3,4-dimethoxybenzyl)-1,2,3,4,5,6,7,8-octahydroisoquinoline raceme and 204 mg of boranamine, where the cell suspension was prepared by resuspending 2.5 g of wet cells collected after centrifugation in 50 mM phosphate buffered saline (pH 7.5). The reaction mixture was reacted at 30° C. and 600 rpm. 68 h later, when the reaction was confirmed by LC to be completed, 1 M hydrochloric acid was introduced to terminate the reaction, and the reaction mixture was adjusted to pH 10 with 3 M sodium hydroxide and extracted three times with ethyl acetate by high-speed centrifugation (100 mL×3). The organic phases were combined, dried with anhydrous sodium sulfate and then purified by column chromatography to give 271 mg of a product (67% yield), where the optical test results showed that the product had $[α]^{25}_D$ of −100.13 (c=0.5, methanol, 1=100 mm). Then the product was analyzed by LC to have an ee value of 97%, where the detection parameters were described as follows: OJ-H column; mobile phase: a mixture of n-hexane and isopropanol (containing 0.5% ethanolamine) in a ratio of 95:5; flow rate: 0.5 mL/min; column temperature: 25° C.; and wavelength: 230 nm.

$^1$H NMR (400 MHz, CDCl$_3$) δ/ppm 6.82-6.73 (m, 3H), 3.88 (s, 3H), 3.86 (s, 3H), 3.28 (d, J=10.4 Hz, 1H), 3.06-2.92 (m, 2H), 2.71 (ddd, J=11.9, 7.6, 5.1 Hz, 1H), 2.47 (dd, J=13.6, 10.4 Hz, 1H), 2.18-2.06 (m, 1H), 1.91 (m, 5H), 1.72 (m, 3H), 1.52 (m, 2H).

$^{13}$C NMR (100 MHz, CDCl$_3$) δ/ppm 148.90, 147.46, 132.34, 129.80, 128.61, 121.21, 112.29, 111.32, 58.72, 55.92, 55.86, 40.87, 38.40, 30.98, 30.45, 26.99, 23.25, 22.83.

Example 5 Preparation of (S)-1-(4-nitrobenzyl)-1,2,3,4,5,6,7,8-octahydroisoquinoline by Enzymatic Kinetic Resolution (40 g/L Substrate)

To 7.5 mL of a cell suspension were added 300 mg of a 1-(4-nitrobenzyl)-1,2,3,4,5,6,7,8-octahydroisoquinoline raceme and 175 mg of boranamine, where the cell suspension was prepared by resuspending 1.5 g of wet cells collected after centrifugation in 50 mM phosphate buffered saline (pH 7.5). The reaction mixture was reacted at 35° C. and 900 rpm. 66 h later, when the reaction was confirmed by LC to be completed, 1 M hydrochloric acid was introduced to terminate the reaction, and the reaction mixture was adjusted to pH 10 with 3 M sodium hydroxide and extracted three times with ethyl acetate by high-speed centrifugation (100 mL×3). The organic phases were combined, dried with anhydrous sodium sulfate and then purified by column chromatography to give 231 mg of a product (77% yield), where the optical test results showed that the product had $[α]^{25}_D$ of −171.48 (c=0.5, methanol, 1=100 mm). Then the product was analyzed by LC to have an ee value of 97%, where the detection parameters were described as follows: OJ-H column; mobile phase: a mixture of n-hexane and isopropanol (containing 0.5% ethanolamine) in a ratio of 95:5; flow rate: 0.5 mL/min; column temperature: 25° C.; and wavelength: 230 nm.

$^1$H NMR (400 MHz, CDCl$_3$) δ/ppm 8.19 (d, J=8.5 Hz, 2H), 7.43 (d, J=8.4 Hz, 2H), 3.38 (d, J=10.4 Hz, 1H), 3.14 (dd, J=13.6, 3.2 Hz, 1H), 3.03 (dt, J=11.4, 5.5 Hz, 1H), 2.78 (ddd, J=12.1, 7.1, 5.1 Hz, 1H), 2.69 (dd, J=13.6, 10.4 Hz, 1H), 2.20-2.07 (m, 1H), 2.06-1.85 (m, 5H), 1.85-1.68 (m, 2H), 1.67-1.45 (m, 3H).

$^{13}$C NMR (100 MHz, CDCl$_3$) δ/ppm 148.40, 146.60, 130.05, 129.44, 123.68, 58.59, 40.62, 39.11, 30.87, 30.47, 27.11, 23.20, 22.77.

Described above are merely preferred embodiments of the invention, which are intended to illustrate the spirit and features of the invention and are not intended to limit the application. Any changes, replacements and modifications made without departing from the spirit of the invention should fall within the scope of the invention.

What is claimed is:

1. A method of preparing a (S)-1-benzyl-1,2,3,4,5,6,7,8-octahydroisoquinoline compound of formula (I)

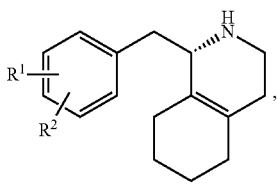

I comprising: subjecting a 1-benzyl-1,2,3,4,5,6,7,8-octahydroisoquinoline racemate as a substrate to the kinetic resolution in the presence of the monoamine oxidase as a catalyst and a non-selective reductant to prepare the (S)-1-benzyl-1,2,3,4,5,6,7,8-octahydroisoquinoline compound;

wherein $R^1$ and $R^2$ are independently selected from the group consisting of hydrogen, $C_1$-$C_6$ alkyl and cycloalkyl, $C_1$-$C_6$ alkoxyl, halogen, cyano, nitro, hydroxyl, amino, methylthio, $C_1$-$C_6$ ester group and trifluoromethyl;

wherein the monoamine oxidase consists of the amino acid sequence of SEQ ID NO: 1; and the non-selective reductant is selected from the group consisting of boronamine and sodium borohydride.

2. The method of claim 1, wherein the monoamine oxidase is obtained using an *E. coli* expression system.

3. The method of claim 1, wherein the non-selective reductant is for reducing an amine.

4. The method of claim 1, wherein a molar equivalent ratio of the non-selective reductant to the 1-benzyl-1,2,3,4,5,6,7,8-octahydroisoquinoline racemate is 1-10:1.

5. The method of claim 1, wherein the 1-benzyl-1,2,3,4,5,6,7,8-octahydroisoquinoline raceme has a concentration of 0.1%-5% (w/v).

6. The method of claim 1, wherein the monoamine oxidase, calculated as wet cells, is 300%-1000% by weight of the 1-benzyl-1,2,3,4,5,6,7,8-octahydroisoquinoline raceme.

7. The method of claim 1, wherein a reaction temperature is 15-50° C.; a reaction time is 6-72 h; and a pH of the reaction mixture is 6-10.

8. The method of claim 1, wherein the monoamine oxidase is in a form of a genetically-engineered whole cell, a crude enzyme solution, a pure enzyme or an immobilized enzyme.

9. The method of claim 1, further comprising: purifying the (S)-1-benzyl-1,2,3,4,5,6,7,8-octahydroisoquinoline compound.

10. The method of claim 9, the purifying step comprises:
terminating the reaction with 1-6 M hydrochloric acid;
adjusting pH of the reaction mixture to 10-11 with 1-10 M sodium hydroxide;
extracting the reaction mixture with ethyl acetate 3-5 times by high-speed centrifugation and collecting and combining organic phases; and
drying the combined organic phase with anhydrous sodium sulfate; and purifying the dried organic phase by column chromatography to give the purified (S)-1-benzyl-1,2,3,4,5,6,7,8-octahydroisoquinoline compound.

* * * * *

SEQUENCE LISTING

<160> NUMBER OF SEQ ID NOS: 1

<210> SEQ ID NO 1
<211> LENGTH: 453
<212> TYPE: PRT
<213> ORGANISM: Artificial Sequence
<220> FEATURE:
<223> OTHER INFORMATION: synthetic

<400> SEQUENCE: 1

```
Met Ser Asn Gln Thr Asp Ala Asp Val Ile Val Ile Gly Ala Gly Pro
1               5                   10                  15

Ser Gly Ser Tyr Ala Ala Lys Leu Leu His Asp Gln Gly Val Arg Val
            20                  25                  30

Lys Leu Val Glu Ala Lys Asp Arg Val Gly Gly Arg Thr Trp Ser Thr
        35                  40                  45

Lys Ser Asp Ala Pro Gly Gly Pro Ile Asp Phe Gly Gly Gln Trp Ile
    50                  55                  60

Gly Glu Thr His Val Leu Leu Pro Glu Leu Gly Ala Glu Leu Gly Leu
65                  70                  75                  80

Glu Thr Val Ser Ser Val Lys Pro Gly Asn Asp Leu Phe Val Phe Asn
                85                  90                  95

Gly Asp Val Glu Val Gly Glu Asp Gln Val Pro Ser Gly Ala Ser
            100                 105                 110

Trp Ala Gly Glu Leu Ser Arg Ser Phe Glu Leu Leu Asp Glu Val Gly
        115                 120                 125

Thr Arg Leu Gly Trp Ala Ala Pro Trp Ala Ser Glu His Val Gly Glu
    130                 135                 140

Leu Asp Ser Met Thr Val Ala Gln Trp Leu Gln Asn Val Gln Ser
145                 150                 155                 160

Ser Glu Val Arg Leu Ile His Glu Val Met Val Asn Ile Leu Asn Gly
                165                 170                 175

Ala Ser Thr Thr Glu Val Ser Met Ala Tyr Trp Ala Tyr Phe Val His
            180                 185                 190

Gln Gly Glu Gly Ile Glu Ser Leu Ile Gly Thr Arg Ser Gly Ala Gln
        195                 200                 205

Val Ala Trp Phe Ile Gly Gly Met Gly Gln Val Thr Glu Leu Ile Ala
    210                 215                 220

Asp Lys Leu Gly Asp Asp Val His Leu Asn Trp Pro Val Thr Arg Ile
225                 230                 235                 240

Glu Gln Asp Pro Thr Gly Val Thr Val Phe Ser Gly Glu Arg Arg Leu
                245                 250                 255

Arg Ala Ser Phe Ala Ile Leu Ala Ala Pro Pro Ser Ala Gly Ser Arg
            260                 265                 270

Leu Ile Phe Asp Pro Pro Leu Pro Pro Lys Arg Ala Gln Leu Gln Ala
        275                 280                 285

Arg Ala Pro Leu Gly Arg Leu Ala Lys Ile Gln Val Arg Tyr Asp Glu
    290                 295                 300

Pro Phe Trp Gln Glu Arg Gly Leu Ser Gly Ala Ala Phe Glu Cys Gly
305                 310                 315                 320

Asp Leu Ala Phe Trp Leu Phe Asp Gly Ser Lys Pro Thr Asp Ser Leu
                325                 330                 335

Ala Thr Ile Val Gly Phe Ile Gly Gly Lys His Leu Asp Ala Trp His
            340                 345                 350

Ala Leu Ser Pro Asn Glu Arg Glu Lys Arg Phe Ile Glu Ile Leu Val
```

|   |   | 355 |   |   |   | 360 |   |   |   | 365 |   |   |
|---|---|---|---|---|---|---|---|---|---|---|---|---|
| Asn | Asn | Phe | Gly | Asp | Lys | Ala | Arg | Asp | Val | Arg | Tyr | Val | His | Glu | Thr |
|   | 370 |   |   |   |   | 375 |   |   |   |   | 380 |   |   |   |   |

| Asp | Trp | Thr | Val | Gln | Pro | Trp | Thr | Gly | Gly | Ala | Pro | Val | Thr | Phe | Met |
| 385 |   |   |   |   | 390 |   |   |   |   | 395 |   |   |   |   | 400 |

| Pro | Thr | Gly | Leu | Leu | Ser | Ser | Ala | Gly | Ser | Ala | Leu | Arg | Glu | Pro | Val |
|   |   |   |   | 405 |   |   |   |   | 410 |   |   |   |   | 415 |   |

| Asp | Arg | Leu | His | Phe | Ala | Gly | Thr | Glu | Ala | Ala | Pro | Met | Trp | Ser | Gly |
|   |   |   | 420 |   |   |   |   | 425 |   |   |   |   | 430 |   |   |

| Tyr | Ile | Glu | Gly | Ala | Leu | Arg | Ala | Gly | Lys | Ile | Ala | Ala | Gly | Asp | Val |
|   |   | 435 |   |   |   |   | 440 |   |   |   |   | 445 |   |   |   |

| Leu | Ala | Arg | Leu | Ala |
|   | 450 |   |   |   |